United States Patent [19]
Thor

[11] Patent Number: 5,192,751
[45] Date of Patent: Mar. 9, 1993

[54] USE OF COMPETITIVE NMDA RECEPTOR ANTAGONISTS IN THE TREATMENT OF URINARY INCONTINENCE

[75] Inventor: Karl B. Thor, Carmel, Ind.

[73] Assignee: Eli Lilly and Company, Indianapolis, Ind.

[21] Appl. No.: 919,480

[22] Filed: Jul. 24, 1992

[51] Int. Cl.$^5$ .................... A61K 31/47; A61K 31/675
[52] U.S. Cl. ...................... 514/82; 514/307; 514/326
[58] Field of Search ............... 514/82, 307, 326

[56] References Cited

U.S. PATENT DOCUMENTS 4,902,695 2/1990 Ornstein ............................ 514/307
4,968,678 11/1990 Ornstein ............................ 514/222.2

OTHER PUBLICATIONS

Hansen, Krogsgaard-Larsen, Med. Res. Rev., 10, 55-94 (1990).
Murphy et al., British J. Pharmacol., 95, 932-938 (1988).
Harrison and Simmonds, British J. Pharmacol., 84, 381-391 (1984).
Schoepp et al., J. Neur. Transm., 85, 131-143 (1991).
DeGroat et al., J. Auton. Nerv. Sys., 3, 135-160 (1981).
Shaw et al., Brain Res., 539, 164-168 (1991).
Maggi et al., Eur. J. Pharmacol., 181, 105-109 (1990).
Yoshiyama et al., Neurosci. Lett., 126, 141-144 (1991).
Vera and Nadelhaft, Neurosci. Lett., 134, 135-138 (1991).
Berger et al., J. Urol., 138, 836-838 (1987).
Bradley, Neurolog., 28, 52-58 (1978).
Yoshiyama et al., Neurosci. Abstract, 16, 437.3 (1990).
Matsumoto et al., Neurosci. Lett., 133, 211-214 (1991).

Primary Examiner—Leonard Schenkman
Attorney, Agent, or Firm—James P. Leeds; Leroy Whitaker

[57] ABSTRACT

The present invention provides a method of treating urinary incontinence in a mammal which comprises administering an effective amount of a competitive NMDA antagonist.

15 Claims, 14 Drawing Sheets

USE OF COMPETITIVE NMDA RECEPTOR ANTAGONISTS IN THE TREATMENT OF URINARY INCONTINENCE

BACKGROUND OF THE INVENTION

A variety of common clinical bladder disorders are characterized by spastic or hyperactive bladder smooth muscle, and the ability to store only small quantities of urine. These dysfunctions range from severe hyperactivity, seen following recovery from major spinal cord damage or spinal transection, to mild bladder detrusor hyperactivity, seen in large numbers of patients and due to a variety of causative factors. The causative factors for this latter group of patients include Parkinsonism, multiple sclerosis, cerebrovascular damage, cerebral arteriosclerosis, central nervous system lesions, and a recurrent bladder infection. The major symptoms of these patients are: frequency, nocturia, urgency, and urge incontinence. The treatment of these patients is generally directed to facilitating urine storage by inhibiting bladder contractility or increasing outlet resistance by enhancing sphincter activity.

Pharmacologic management is usually the first type of treatment attempted. A variety of pharmacologic agents have been used to treat these patients, including muscarinic anticholinergics, tricyclic antidepressants, calcium antagonists, $\beta$-andrenergic agonists, and prostaglandin inhibitors. Anticholinergic agents, such as propantheline, oxybutynin, or dicyclomine, alone or in combination with a tricyclic antidepressant, such as imipramine, have proven useful in some patients with bladder hyperactivity. However, nearly 50% of these patients have little or no response to present pharmacological therapies. The consequences of therapeutic failure are costly, and often require serious surgical procedures, such as bladder over-distension, peripheral bladder denervation, or selective sacral rhizotomy. The need for novel pharmacologic approaches for management of these patients is generally agreed upon by urologists.

Incontinence is divided into two types, urge and stress. The urge incontinence type has been further divided into two subtypes in the classical literature, motor urge incontinence and sensory urge incontinence. Motor urge incontinence implies that there is excessive excitatory efferent input to the sacral spinal micturition center from supraspinal centers. Motor urge incontinence accompanies Parkinsonism, multiple sclerosis, cerebrovascular damage, cerebral arteriosclerosis, and central nervous system lesions. Sensory urge incontinence implies excessive sensory input to the sacral spinal micturition center from the bladder primary afferent fibers. Sensory urge incontinence typically accompanies spinal cord injury and bladder infection.

The excitatory amino acids are an important group of neurotransmitters that mediate excitatory neurotransmission in the central nervous system. Glutamic acid and aspartic acid are two endogenous ligands that activate excitatory amino acid (EAA) receptors. There are two types of EAA receptors, ionotropic and metabotropic, which differ in their mode of signal transduction. There are at least three distinct ionotropic EAA receptors characterized by the selective agonist that activate each type: the NMDA (N-methyl-D-aspartic acid), the AMPA (2-amino-3-(5-methyl-3-hydroxyisoxazol-4-yl)propanoic acid), and the kainic acid receptors. The ionotropic EAA receptors are linked to ion channels that are permeable to sodium, and, in the case of NMDA receptors, calcium. Metabotropic receptors, linked to phosphoinositide-hydrolysis by a membrane associated G-protein, are activated by quisqualic acid, ibotenic acid, and (1S,3R)-1-aminocyclopentane 1,3-dicarboxylic acid.

The NMDA receptor is a macromolecular complex consisting of a number of distinct binding sites that gate an ion channel permeable to sodium and calcium ions. Hansen and Krogsgaard-Larsen, Med. Res. Rev., 10, 55–94 (1990). There are binding sites for glutamic acid, glycine, and polyamines, and a site inside the ion channel where compounds such as phencyclidine (PCP) and MK-801 exert their antagonist effects.

Competitive NMDA antagonists are compounds which block the NMDA receptor by interacting with the glutamate binding site. The ability of a particular compound to competitively bind to the NMDA glutamate receptor is determined using a radioligand binding assay. See Murphy et al., British J. Pharmacol., 95, 932–938 (1988). The antagonists are distinguished from the agonists using a rat cortical wedge assay. See Harrison and Simmonds, British J. Pharmacol., 84, 381–391 (1984). Examples of competitive NMDA antagonists include D-2 amino 5-phosphonopentanoic acid (D-AP5), D-2-amino-7-phosphonoheptanoic acid (D-AP7), CGS19775, CPPene, and CGP37849. Schoepp et al., J. Neur. Transm., 85, 131–143 (1991).

Antagonists of neurotransmission at NMDA receptors may prove to be useful therapeutic agents for the treatment of neurological disorders. U.S. Pat. No. 4,902,695 is directed to series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. U.S. Pat. No. 4,968,878 is directed to a second series of competitive NMDA receptor antagonists useful for the treatment of similar neurological disorders and neurodegenerative disorders.

Bladder activity is controlled by parasympathetic preganglionic neurons in the sacral spinal cord. DeGroat et al., J. Auton. Nerv. Sys., 3, 135–160 (1981). In humans, it has been shown that the highest density of NMDA receptors in the spinal cord are located at the sacral level, including those areas that putatively contain bladder parasympathetic preganglionic neurons. Shaw et al., Brain Res., 539, 164–168 (1991). Because NMDA receptors are excitatory in nature, pharmacological blockade of these receptors would suppress bladder activity. Recent studies have shown that MK-801, a non-competitive NMDA antagonist, increases the volume necessary to elicit micturition and decreases the amplitude of the micturition contraction. Maggie et al., Eur. J. Pharmacol, 181, 105–109 (1990); Yoshiyama et al., Neurosci. Lett., 126, 141–144 (1991). However, these studies have shown that the inhibitory effects of MK-801 are not stereospecific, suggesting that nonspecific effects of MK-801 mediated the bladder inhibition. Also, these studies have shown that MK-801 produces endocrine effects that are dissociated from its NMDA antagonism. A separate study has shown that the administration of MK-801 to conscious, freely-moving rats produces an increase in the frequency of micturition. Vera and Nadelhaft, Neurosci. Lett., 134, 135–138 (1991).

SUMMARY OF THE INVENTION

The present invention provides a novel method of treating motor urge urinary incontinence in mammals, which comprises administering to a mammal in need of treatment thereof an effective amount of a competitive NMDA antagonist. One group of competitive NMDA antogonists that can be used in the present invention are the compounds of Formula I

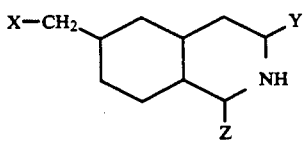

wherein
X is $CO_2H$, $CO_2R^3$, $CON(R^4)_2$, $CONHSO_2R^4$, $CONHCO_2R^3$, $SO_3R^3$, $PO_3(R^R)_2$, or

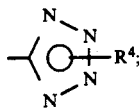

one of Y and Z is $CO_2H$, $CO_2R^3$, $CON(R^4)_2$, $CONHSO_2R^4$, $CONHCO_2R^3$, or

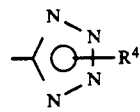

and the other of Y and Z is hydrogen;

each $R^3$ is independently $C_1$-$C_{16}$ alkyl; phenylsubstituted $C_1$-$C_4$ alkyl; benzyl; benzyl substituted on the phenyl ring with halogen, $C_1$-$C_4$ alkyl, or $C_1$-$C_4$ alkoxy; $C_1$-$C_5$ alkanoyloxymethyl; or $C_1$-$C_5$ alkanoyloxymethyl substituted on the oxymethyl with $C_1$-$C_4$ alkyl or $C_4$-$C_7$ cycloalkyl;

each $R^4$ is independently hydrogen, $C_1$-$C_{16}$ alkyl, phenyl-substituted $C_1$-$C_4$ alkyl, or phenyl; or a pharmaceutically acceptable salt thereof.

A second group of competitive NMDA antagonists that can be used in the present invention are the compounds of Formula II.

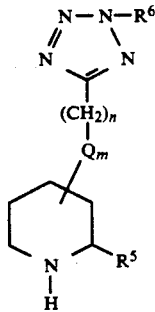

wherein
the compound is in the 2R form;
$R^5$ is $CO_2R^7$, $CON(R^8)_2$, $CONHSO_2R^7$, $CONHCOR^7$, or

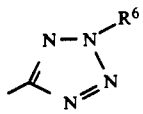

$R^6$ is hydrogen or $C_1$-$C_3$ alkyl;
n is 0, 1, 2, or 3;
m is 0 or 1;
$R^7$ is hydrogen, $CC_1$-$C_4$ alkyl, phenyl, or an oral ester forming group;
Q is CH≡;
each $R^8$ is independently hydrogen, $C_1$-$C_4$ alkyl, or phenyl; or
a pharmaceutically acceptable salt thereof.

DETAILED DESCRIPTION OF THE INVENTION

Figure 1:
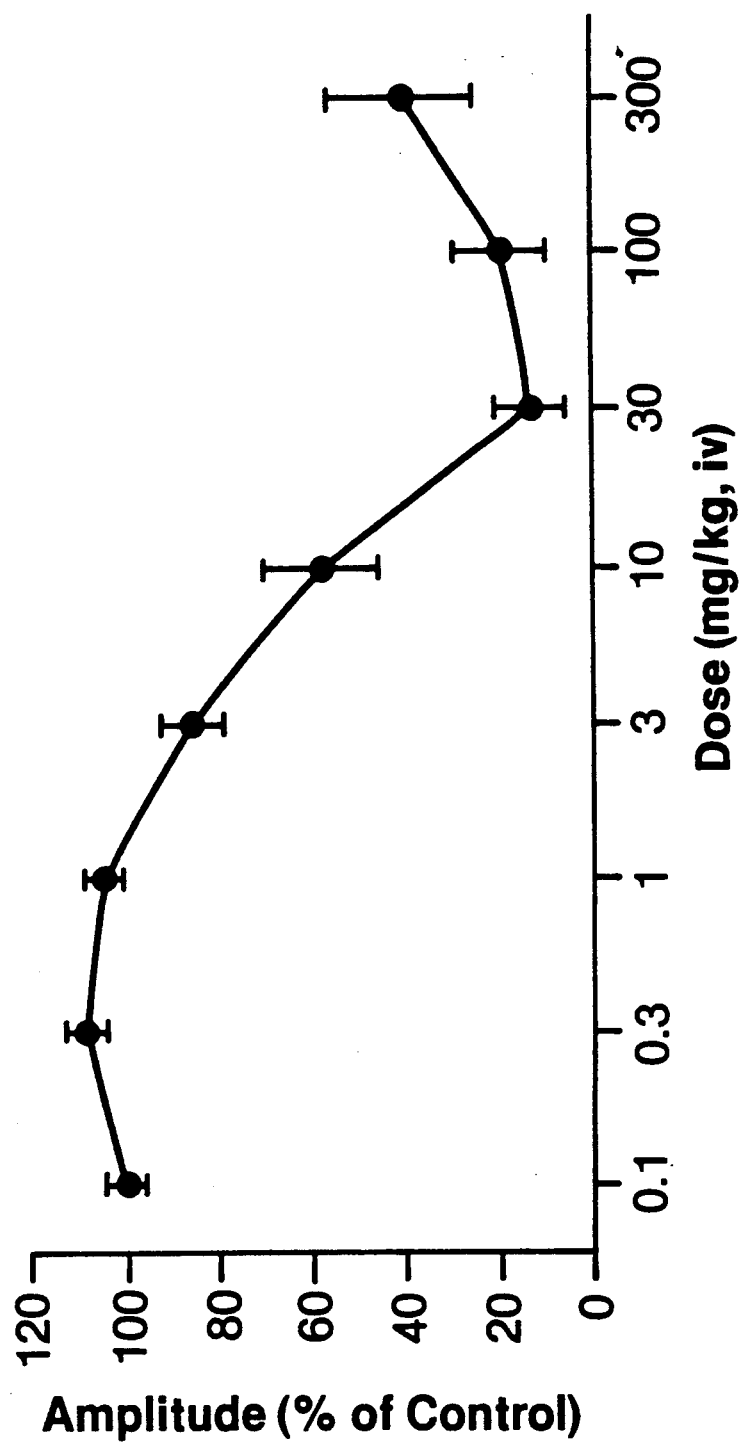
FIG. 1. The effect of compound 1 on the amplitude of the bladder contractions after intravenous administration.

The term "competitive NMDA antagonist" represents a compound which blocks the NMDA receptor by interacting with the glutamate binding site of the NMDA receptor.

The term "$C_1$-$C_{16}$ alkyl" represents a straight or branched alkyl chain having from one to sixteen carbon atoms. Typical $C_1$-$C_{16}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, undecyl, hexadecyl, and the like. The term "$C_1$-$C_{16}$ alkyl" includes within it the terms "$C_1$-$C_6$ alkyl", "$C_1$-$C_4$ alkyl", and "$C_1$-$C_3$ alkyl".

The term "phenyl-substituted $C_1$-$C_4$ alkyl" represents a $C_1$-$C_4$ alkyl group bearing a phenyl group, such as benzyl, 1-phenylethyl, 2-phenylethyl, 3-phenylpropyl, 4-phenylbutyl, 2-methyl-2-phenylpropyl and the like. The term "phenyl-substituted $C_1$-$C_4$ alkoxy" represents a $C_1$-$C_4$ alkoxy group bearing a phenyl group, such as 1-phenylmethoxy, 1-phenylethoxy, 2-phenylethoxy, 3-phenylpropoxy, 4-phenylbutoxy, 2-methyl 2-phenylpropoxy and the like.

The term "oral ester forming group" represents a substituent which, when attached to the carboxylic acid group, forms an ester function suitable for administration to mammals needing treatment thereof. Examples of such oral ester forming groups include $C_1$-$C_4$ alkyl; benzyl; benzyl substituted on the phenyl ring with halogen, $C_1$-$C_4$ alkyl, or $C_1$-$C_4$ alkoxy; $C_1$-$C_5$ acyloxymethyl; or $C_1$-$C_5$ acyloxymethyl substituted on the oxymethyl with $C_1$-$C_4$ alkyl or $C_4$-$C_7$ cycloalkyl. In particular, examples of such groups include: methyl, ethyl, n-propyl, i-propyl, n-butyl, secbutyl, t-butyl, and the like; benzyl; 2-chlorobenzyl, 3-chlorobenzyl, 4-chlorobenzyl, 2,3-dichlorobenzyl, 3,4-dichlorobenzyl, 2-methylbenzyl, 3-methylbenzyl, 4-methylbenzyl, 2,3-dimethylbenzyl, 3,4-dimethylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, and the like; acetoxymethyl, and the like; α-acetoxyethyl, acetoxy(cyclohexyl)methyl, and the like.

The Formula I and Formula II compounds are believed to be competitive NMDA antagonists. The Formula I compounds are described in U.S. Pat. No. 4,902,695 (Feb. 20, 1990), which is incorporated herein by reference. The Formula II compounds are described in U.S. Pat. No. 4,968,678 (Nov. 6, 1990), which is incorporated herein by reference.

While all the Formula I and Formula II compounds are believed to be useful for the treatment of motor urge incontinence, there are certain compounds which are preferred for such use. For the Formula I compounds, preferably, X is $CO_2H$, $PO_3(R^4)_2$, or tetrazole; Y is hydrogen, $CO_2R^3$, or $CO_2H$; Z is hydrogen or $CO_2H$; $R^3$ is $C_1$-$C_{16}$ alkyl, benzyl, or $C_1$-$C_5$ alkanoyloxymethyl; and $R^4$ is hydrogen or methyl; or a pharmaceutically acceptable salt thereof. More preferably, X is $CO_2H$, $PO_3H_2$, or tetrazole; Y is $CO_2R^3$ or $CO_2H$; Z is hydrogen and $R^3$ is $C_1$-$C_{16}$ alkyl, benzyl, or $C_1$-$C_5$ alkanoyloxymethyl; or a pharmaceutically acceptable salt thereof. The most preferred Formula I compounds are those compounds where X is $PO_3H_2$ or tetrazole, Y is $CO_2H$, and Z is hydrogen, or a pharmaceutically acceptable salt thereof. For the Formula II compounds, preferably, $R^5$ is $CO_2R^7$; $R^6$ is hydrogen or methyl; $R^7$ is hydrogen, $C_1$-$C_4$ alkyl, or phenyl; m is 0 or 1; and n is 1, 2, or 3; or a pharmaceutically acceptable salt thereof. More preferably, $R^5$ is $CO_2H$; $R^6$ is hydrogen; m is 0; and n is 1, 2, or 3; or a pharmaceutically acceptable salt thereof. The most preferred Formula II compounds are those where $R^5$ is $CO_2H$, $R^6$ is hydrogen, m is 0, and n is 1, or a pharmaceutically acceptable salt thereof. Other preferred aspects of the present invention will be noted hereinafter.

The Formula I and Formula II compounds possess more than one asymmetric center. Therefore, the compounds can exist as diastereomers, each of which can exist as the racemic mixture of enantiomers. The Formula I compounds possess four asymmetric carbon atoms represented by the carbon atom bearing Y or Z, the carbon atom bearing the $CH_2X$ group, and the two bridgehead carbon atoms. For the preferred group of Formula I compounds, the preferred configuration of the diastereomer is 3SR,4aRS,6SR,8aRS and the preferred configuration of enantiomer is 3S,4aR,6S,8aR. The Formula II compounds possess two asymmetric carbon atoms represented by the carbon atom of the piperidine ring which bears the tetrazole ring and the carbon atom of the ring bearing $R^1$. For the Formula II compounds, the preferred configuration of the diastereomer is 2SR,4RS for the 2,4 cis substituted compounds and 2SR,4SR for the 2,4 trans substituted compounds. The more preferred configuration of the diastereomer is 2SR,4RS. The preferred configuration of the enantiomer is 2R,4S. The preferred relative stereochemistry of the Formula I and Formula II compounds is illustrated in the Table.

TABLE

Examples of Formula I and Formula II Compounds

| Compound No. | Structure |
|---|---|
| 1 | $H_2O_3P$-(cyclohexane ring with H substituents)-$CO_2H$, NH |
| 2 | (tetrazole)-$N=N$, $N-N$-(cyclohexane ring with H substituents)-$CO_2H$, NH |
| 3 | (tetrazole N-N, N-N)-(piperidine ring with H)-$CO_2H$, NH |

The term "effective amount" as used herein, represents an amount of a Formula I or Formula II compound, or a pharmaceutically acceptable salt thereof, which is capable of facilitating urine storage by inhibiting bladder contractility. The particular dose of the compound administered will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, intranasal, intrathecal routes. A typical daily dose will contain from about 0.05 mg/kg to about 80 mg/kg of the active compound. Preferred daily doses will be about 0.1 to about 50 mg/kg, ideally about 0.1 to about 25 mg/kg.

The following experiments were conducted to demonstrate the ability of competitive NMDA antagonists to treat urinary incontinence. Experiments were performed on female Sprague-Dawley rats (300-360 g) anesthetized with urethane (1.2 g/kg given i.p. or s.c.). The trachea was cannulated with a polyethylene tube (PE205) to maintain a patent airway. Cannulae were placed in the external jugular vein for intravenous drug administration and in the carotid or femoral artery for blood pressure recording. A transurethral bladder catheter connected to a pressure transducer was used to record bladder pressure isovolumetrically and to distend the bladder with physiological saline or acetic acid. Changes in bladder activity and sphincter activity were recorded and expressed as pressure (cm $H_2O$) and firing rate (spikes per second). Data were normalized and drug effects expressed as a percent of the control activity. In some animals, the spinal cords were transected at the T13 level one week prior to drug administration.

Bladder activity was recorded under constant isovolumetric conditions. For the control experiments, bladder activity consisted of rhythmic contractions occurring at a frequency of 0.25 to 1.6 per minute with a duration of 12 to 6 seconds in a peak amplitude of 22-160 cm $H_2O$. The amplitude of bladder contractions decreased in a dose-dependent fashion following the administration of the competitive NMDA receptor antagonist. The administration of the competitive NMDA antagonist also produced a dose-dependent inhibition of sphincter activity.

Figure 2:
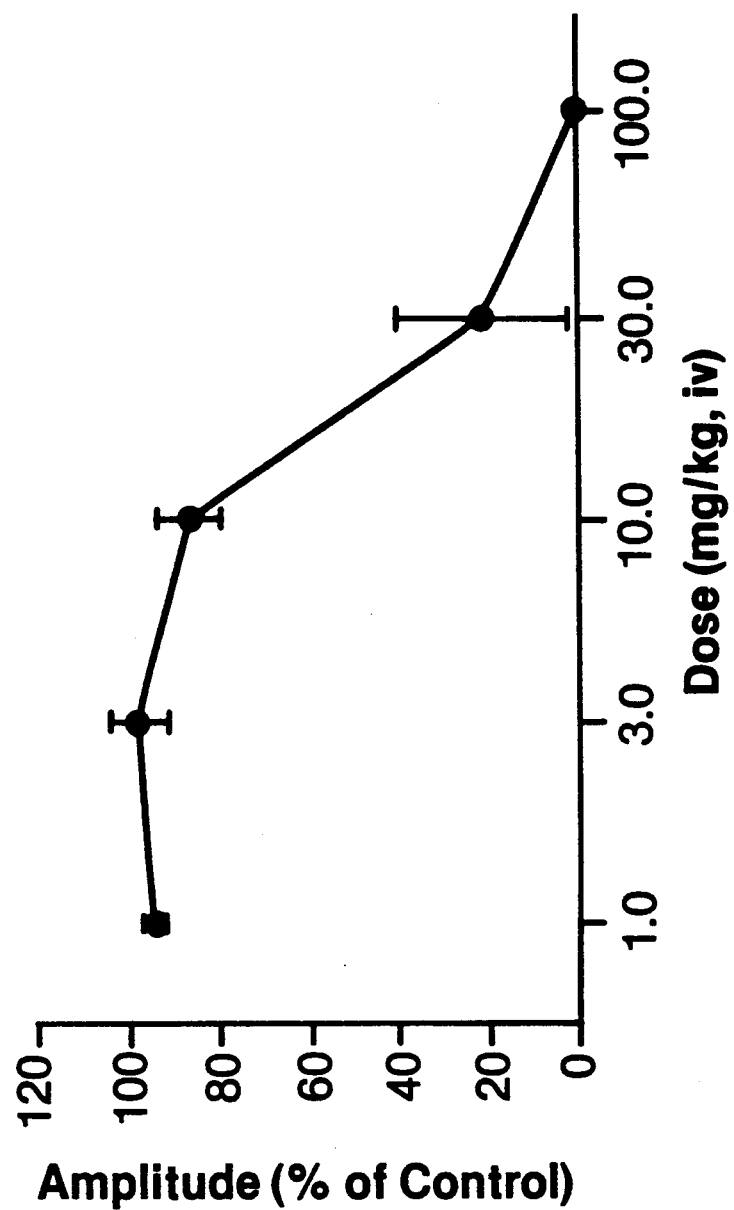
FIG. 2. The effect of compound 2 on the amplitude of the bladder contractions after intravenous administration.
Figure 3:
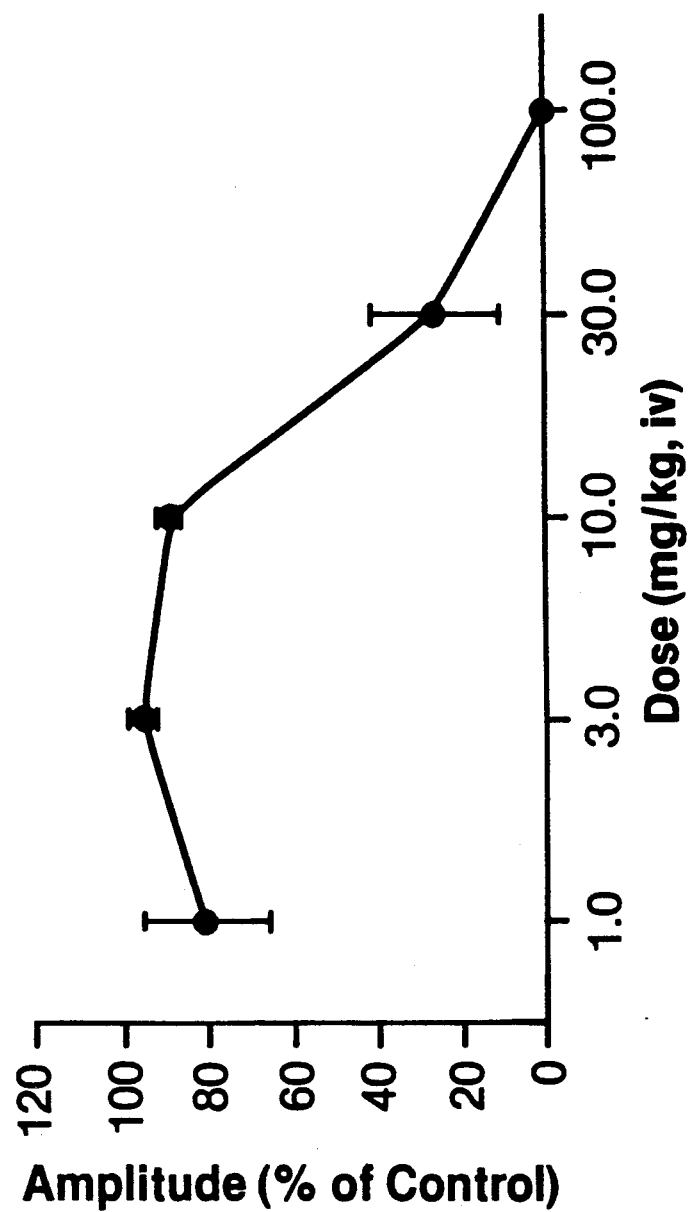
FIG. 3. The effect of compound 3 on the amplitude of the bladder contractions after intravenous administration.
Figure 4:
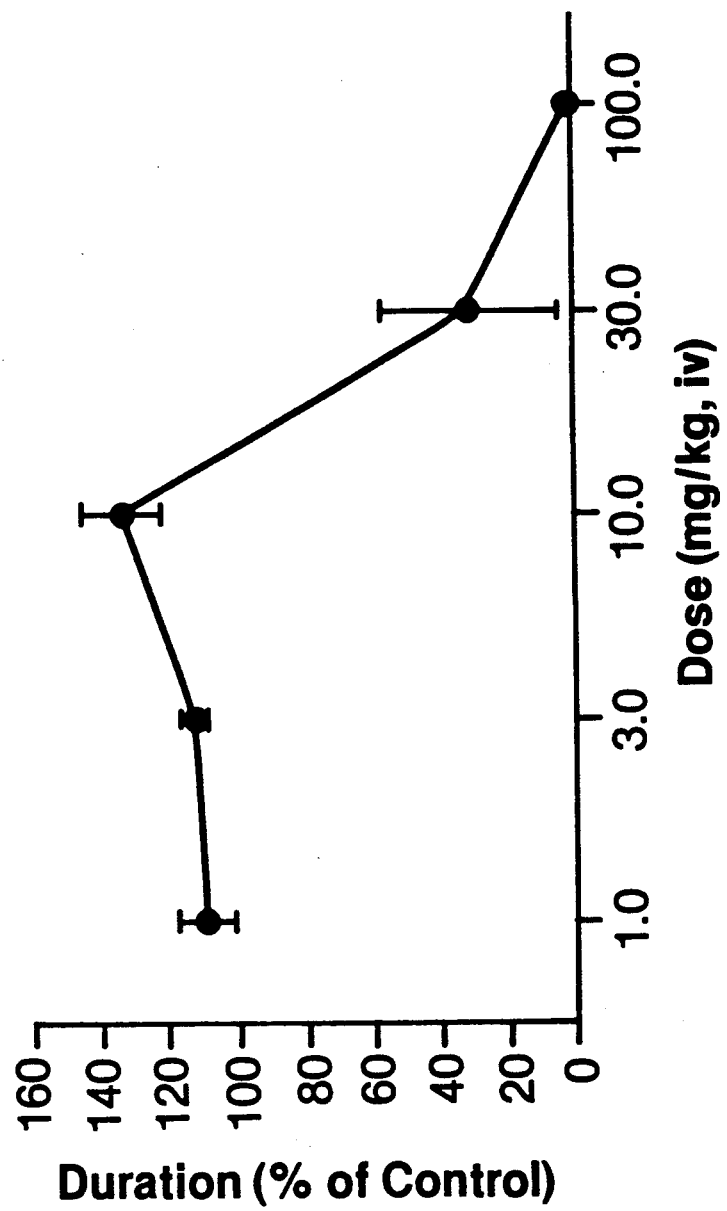
FIG. 4. The effect of compound 2 on the duration of the bladder contractions after intravenous administration.
Figure 5:
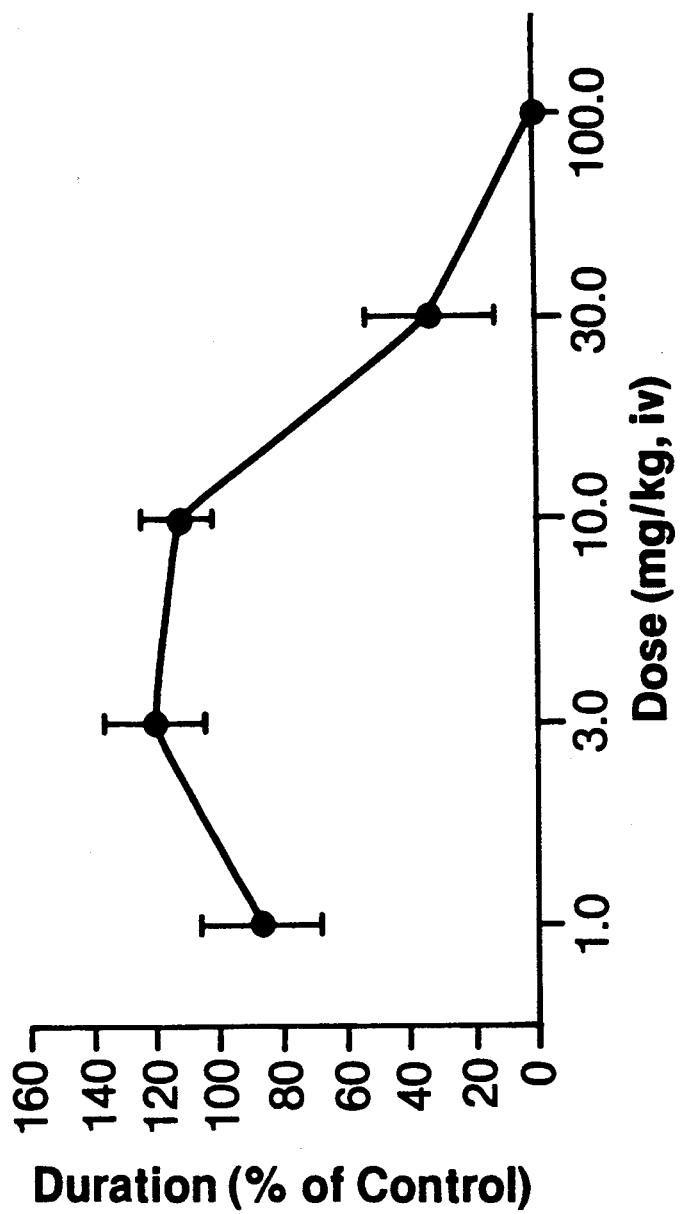
FIG. 5. The effect of compound 3 on the duration of the bladder contractions after intravenous administration.
Figure 6:
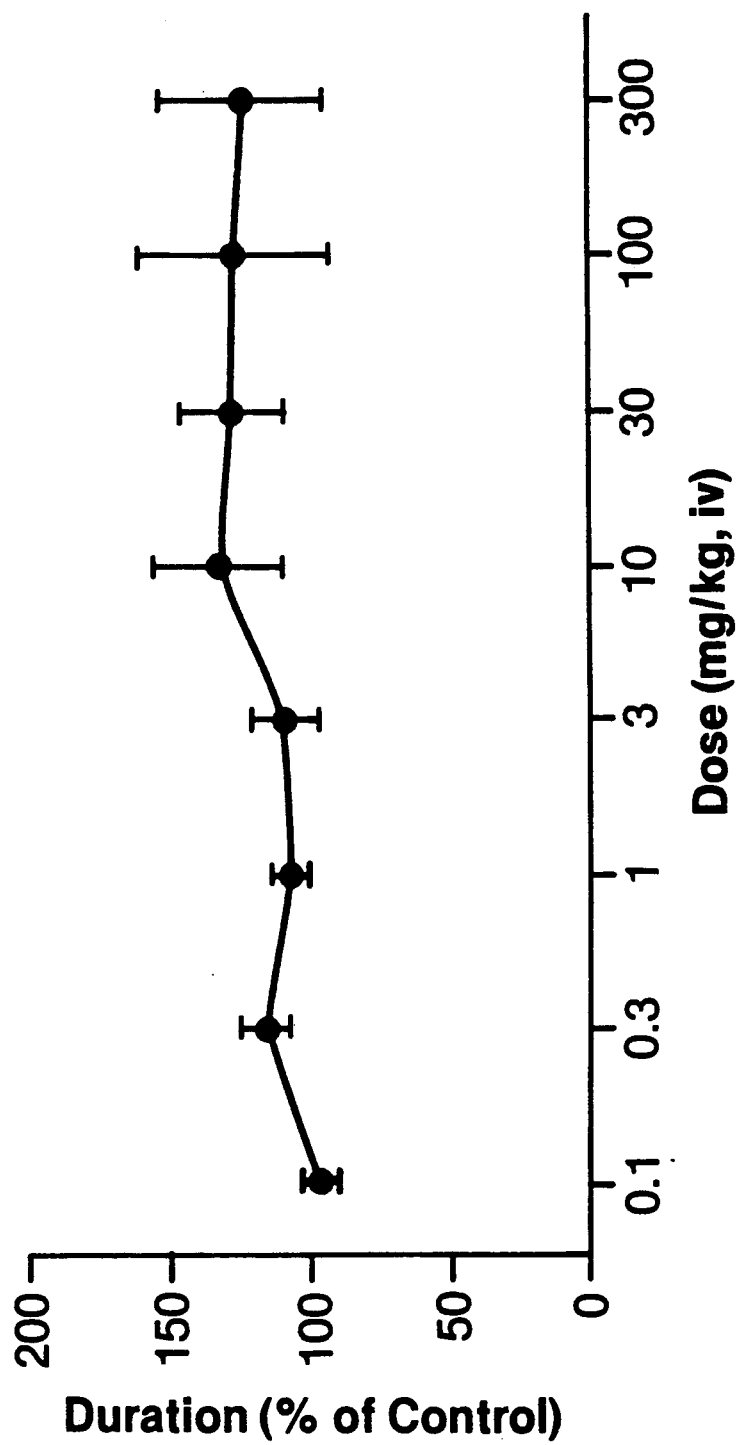
FIG. 6. The effect of compound 1 on the duration of the bladder contractions after intravenous administration.
Figure 7:
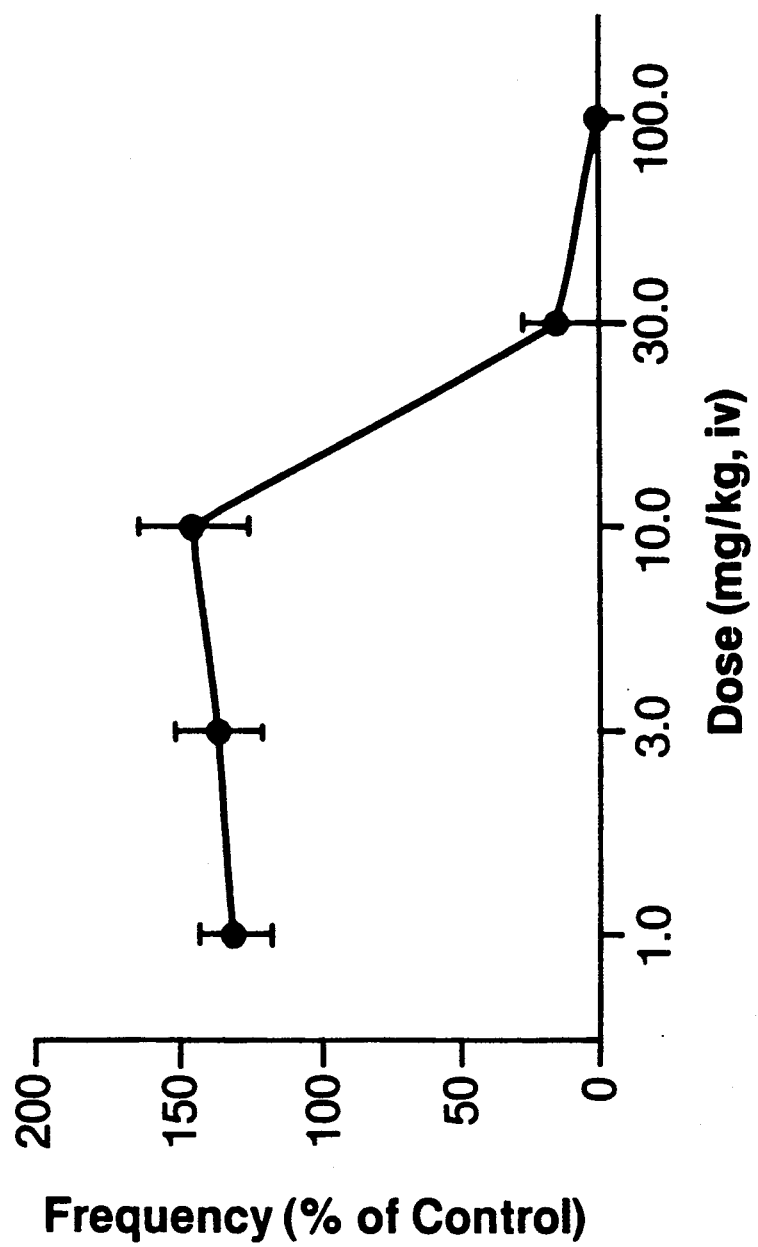
FIG. 7. The effect of compound 2 on the frequency of the bladder contractions after intravenous administration.
Figure 8:
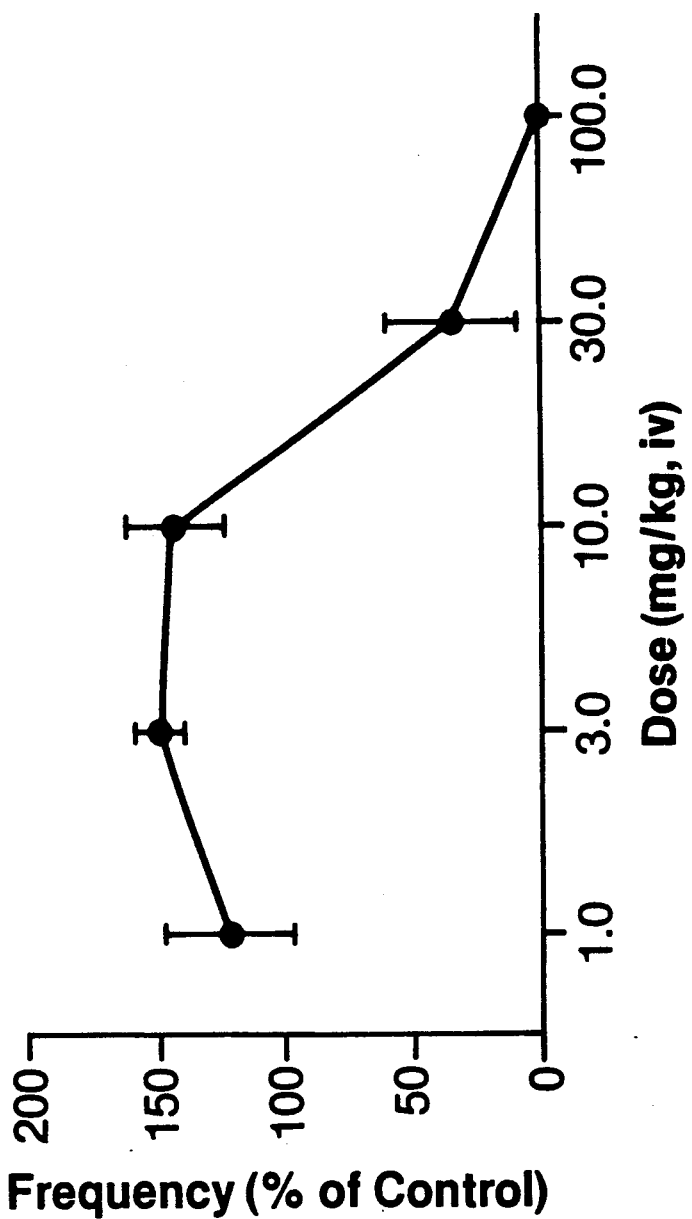
FIG. 8. The effect of compound 3 on the frequency of the bladder contractions after intravenous administration.
Figure 9:
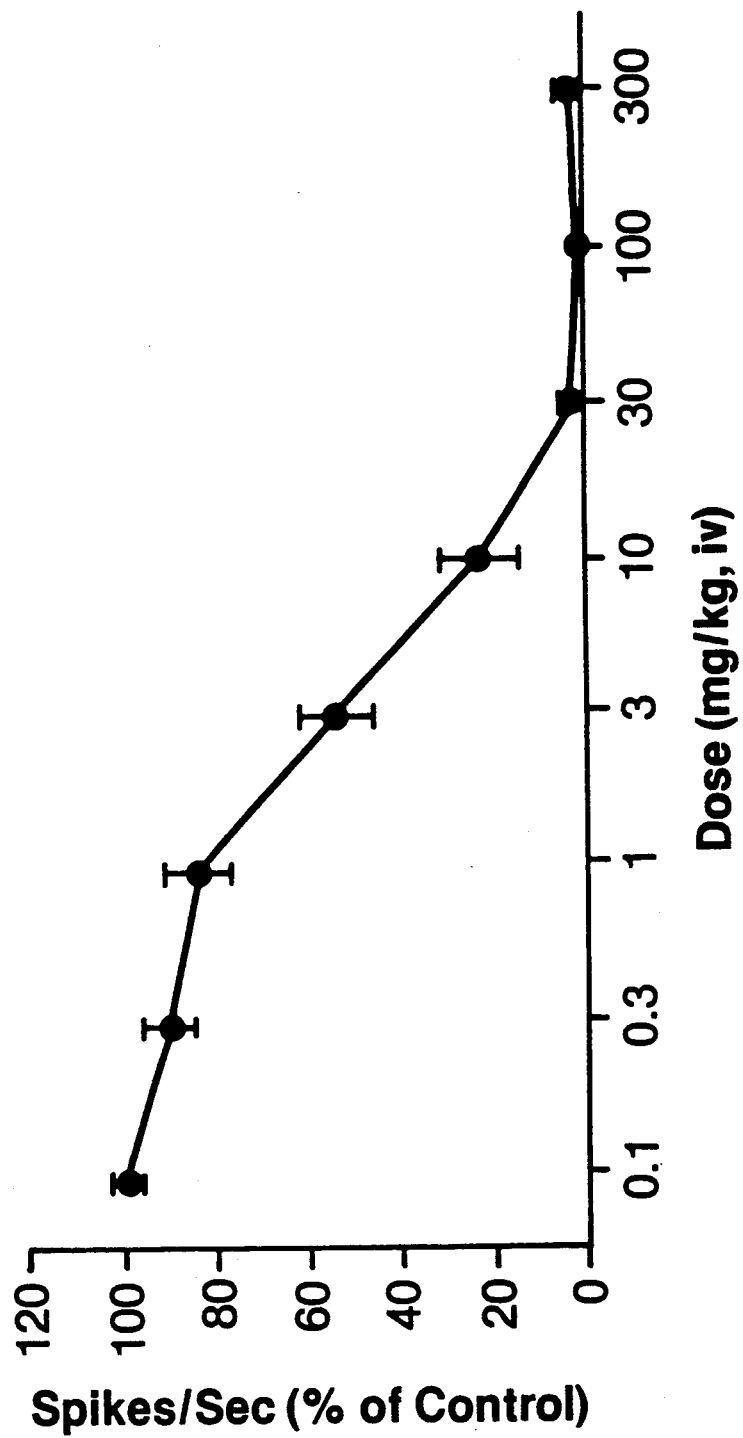
FIG. 9. The effect of compound 1 on the external urethral sphincter activity after intravenous administration.
Figure 10:
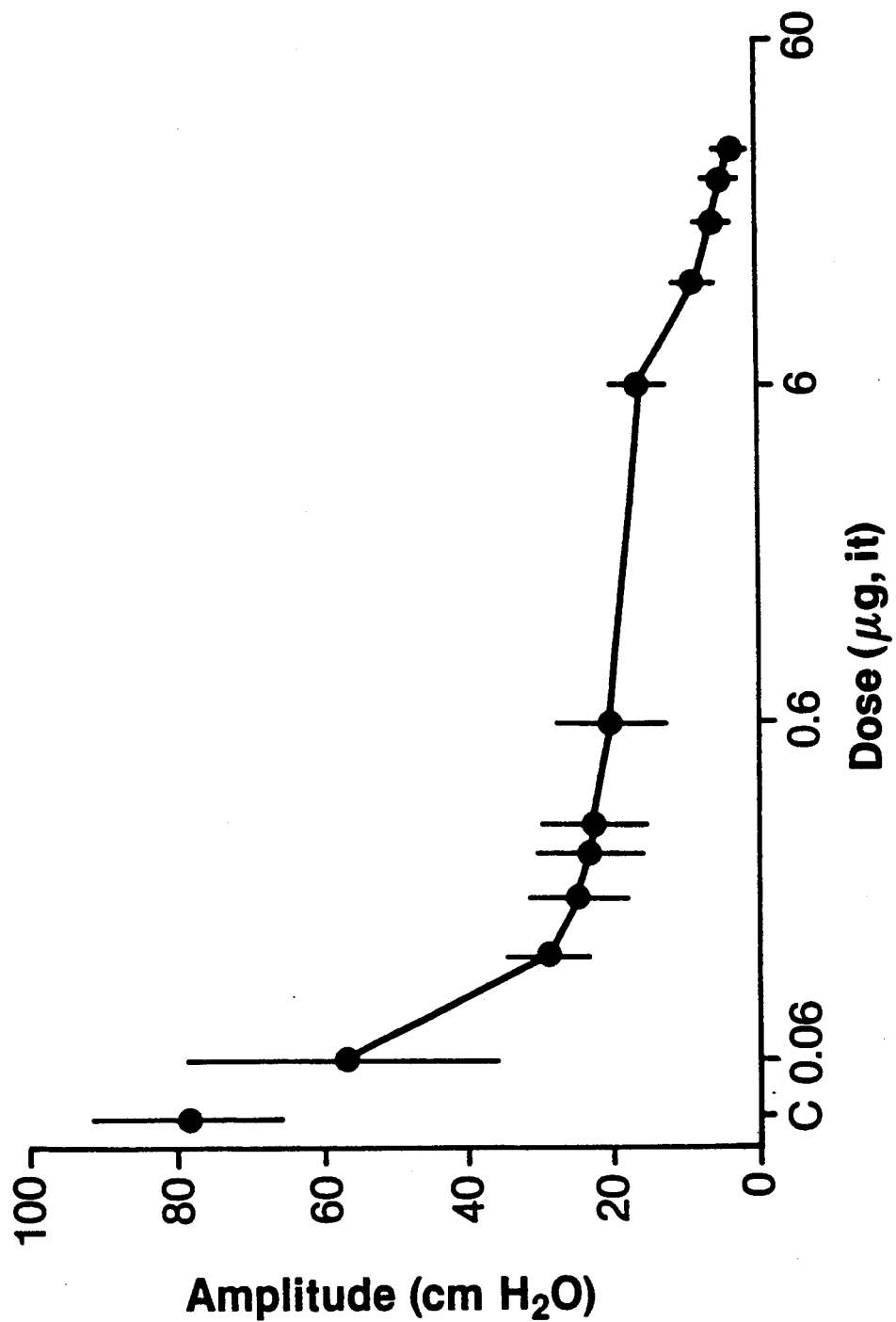
FIG. 10. The effect of compound 1 on the amplitude of the bladder contractions after intrathecal administration.
Figure 11:
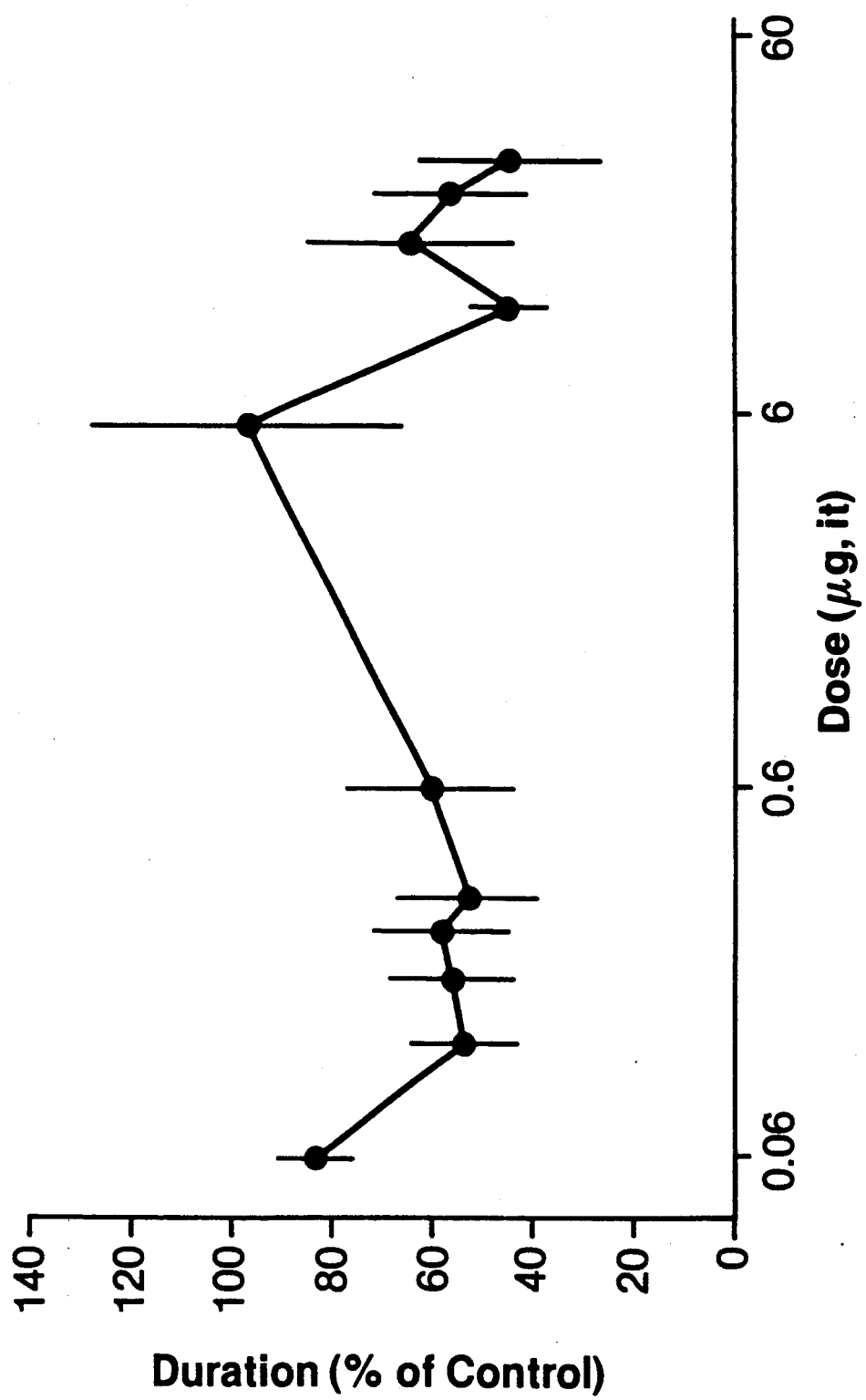
FIG. 11. The effect of compound 1 on the duration of the bladder contractions after intrathecal administration.
Figure 12:
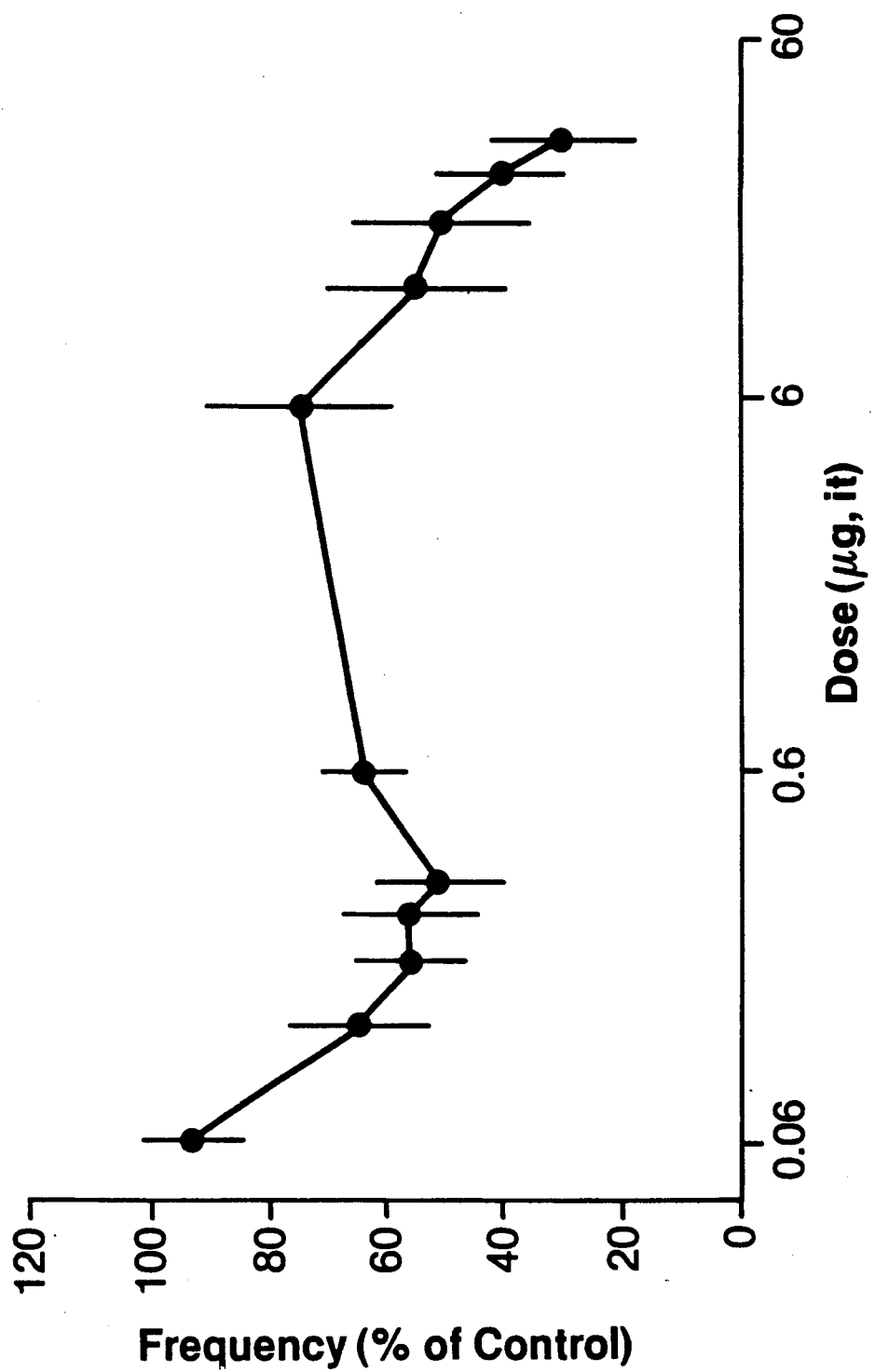
FIG. 12. The effect of compound 1 on the frequency of the bladder contractions after intrathecal administration.
Figure 13:
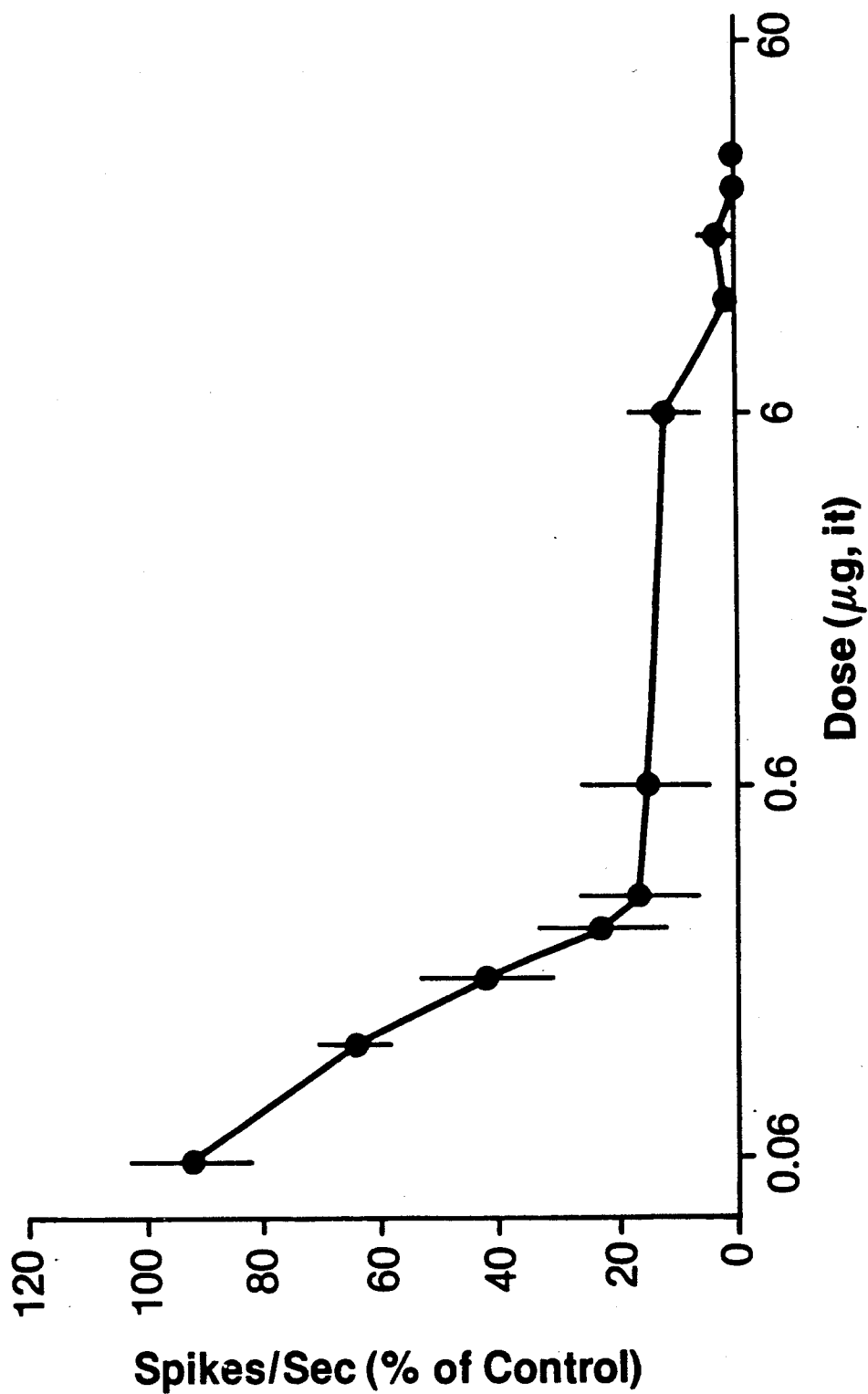
FIG. 13. The effect of compound 1 on the external urethral sphincter activity after intrathecal administration.

In particular, in rats with saline-infused bladders, intravenous (i.v.) administration of compounds 1, 2, and 3 produced a dose-dependent inhibition of the amplitude of the bladder contractions (FIGS. 1, 2, and 3). Administration of compounds 2 and 3 also produced a dose-dependent decrease in the duration of the bladder contractions (FIGS. 4 and 5); however, administration of compound 1 had little effect on the duration of the contractions (FIG. 6). Administration of compounds 2 and 3 also produced a dose-dependent decrease in the frequency (increase in the capacity) of the bladder contractions (FIGS. 7 and 8). Intravenous administration of compound 1 produced a dose dependent inhibition of external urethral sphincter (EUS) activity (FIG. 9). This competitive NMDA antagonist also inhibited both bladder and sphincter activity following direct intrathecal (i.t.) administration to the spinal cord (FIGS. 10, 11, 12, and 13). However, this competitive NMDA antagonist, compound 1, was ineffective in suppressing bladder activity in animals with acetic acid-infused bladders.

Figure 14:
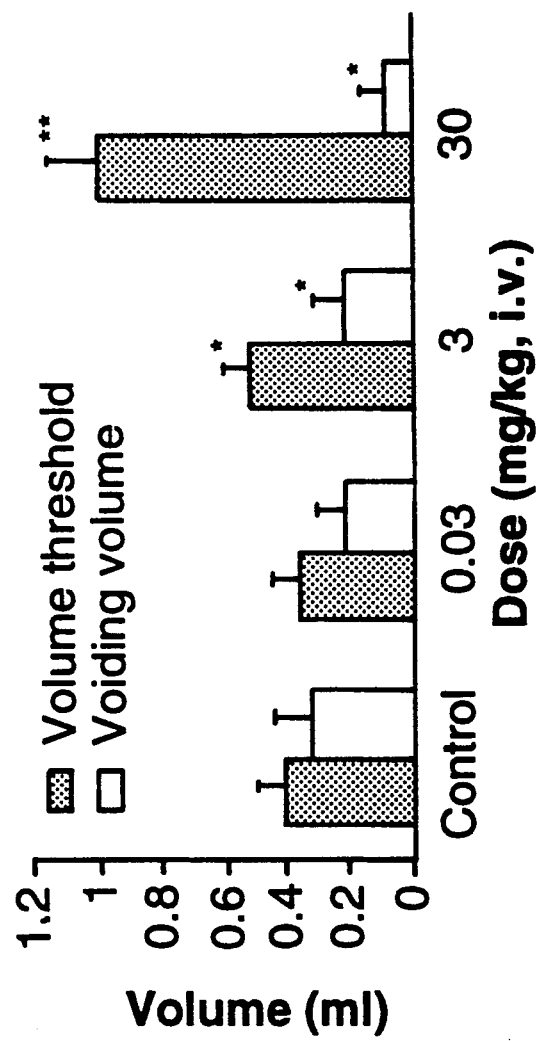
FIG. 14. The effect of compound 1 on threshold volume and voiding volume after intravenous administration.

The effect of the competitive antagonists on the capacity of the bladder was determined by the following experiment. The bladder of the test animal was emptied, and then slowly infused with saline (0.04 ml/min). The volume that is required to cause release of a portion of the bladder's contents is the threshold volume (capacity); the volume of fluid that is released is the voiding volume. Intravenous administration of compound 1 produced a dose-dependent increase in the threshold volume and a dose-dependent decrease in the voiding volume (FIG. 14).

These experiments show that competitive NMDA antagonists produced a dose-dependent inhibition of bladder and of urethral sphincter activity following intravenous administration to mammals. The Formula I and II compounds also produced inhibition after intrathecal administration, indicating a spinal site of action. Unfortunately, these compounds were ineffective in inhibiting acetic acid-induced bladder contractions. The difference between the compounds ability to suppress saline-infused bladder activity and the ability to suppress acetic acid-infused bladder activity reflects the difference between the central organization of the reflex pathways that mediate bladder activity under these circumstances. The saline-infused bladder activity is mediated by a spinobulbospinal reflex pathway that is dependent upon supraspinal inputs from the pons, which in turn activate the parasympathetic preganglionic neurons. In contrast, acetic acid-induced bladder activity is mediated by a purely spinal reflex pathway that is independent of supraspinal structures. Therefore, the competitive NMDA antagonists are useful for the treatment of motor urge incontinence, where cortical or subcortical inhibitory centers have been damaged or compromised by neurological disorders, for example, stroke, Parkinson's Disease, multiple sclerosis, or cerebral arterial sclerosis. Berger et al., J. Urol., 138, 836-838 (1987); Bradley, Neurology. 28, 52-58 (1978).

I claim:

1. A method of treating motor urge urinary incontinence in mammals which comprises administering to a mammal in need of treatment therefor an effective amount of a competitive NMDA antagonist.

2. The method of claim 1 wherein the competitive NMDA antagonist is a compound of the formula

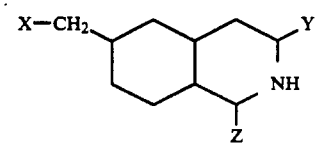

wherein:
X is $CO_2H$, $CO_2R^3$, $CON(R^4)_2$, $CONHSO_2R^4$, $CONHCO_2R^3$, $SO_3R^3$, $PO_3(R^4)_2$, or

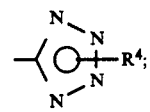

one of Y and Z is $CO_2H$, $CO_2R^3$, $CON(R^4)_2$, $CONHSO_2R^4$, $CONHCO_2R^3$, or

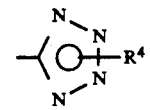

and the other of Y and Z is hydrogen;
each $R^3$ is independently $C_1$-$C_{16}$ alkyl; phenyl-substituted $C_1$-$C_4$ alkyl; benzyl; benzyl substituted phenyl ring with halogen, $C_1$-$C_4$ alkyl, or $C_1$-$C_4$ alkoxy; $C_1$-$C_5$ alkanoyloxymethyl; or $C_1$-$C_5$ alkanoyloxymethyl substituted on the oxymethyl with $C_1$-$C_4$ alkyl or $C_4$-$C_7$ cycloalkyl;
each $R^4$ is independently hydrogen, $C_1$-$C_{16}$ alkyl, phenyl-substituted $C_1$-$C_4$ alkyl, or phenyl; or a pharmaceutically acceptable salt thereof.

3. The method of claim 2 wherein X is $CO_2H$, $PO_3(R^4)_2$, or tetrazole; Y is hydrogen, $CO_2R^3$, or $CO_2H$; Z is hydrogen or $CO_2H$; $R^3$ is $C_1$–$C_{16}$ alkyl, benzyl, or $C_1$–$C_5$ alkanoyloxymethyl; and $R^4$ is hydrogen or methyl; or a pharmaceutically acceptable salt thereof.

4. The method of claim 3 wherein X is $CO_2H$, $PO_3H_2$, or tetrazole; Y is $CO_2R^3$ or $CO_2H$; Z is hydrogen; and $R^3$ is $C_1$–$C_{16}$ alkyl, benzyl, Or $C_1$–$C_5$ alkanoyloxymethyl; or a pharmaceutically acceptable salt thereof.

5. The method of claim 4 wherein X is $PO_3H_2$ or tetrazole, Y is $CO_2H$, and Z is hydrogen, or a pharmaceutically acceptable salt thereof.

6. The method of claim 2 wherein the competitive NMDA antagonist is (3SR,4aRS,6SR,8aRS)-decahydro-6-(phosphonomethyl)-3-isoquinolinecarboxylic acid, or a pharmaceutically acceptable salt thereof.

7. The method of claim 2 wherein the competitive NMDA antagonist is (3S,4aR,6S,8aR)-decahydro-6-(phosphonomethyl)-3 isoquinolinecarboxylic acid, or a pharmaceutically acceptable salt thereof.

8. The method of claim 2 wherein the competitive NMDA antagonist is (3SR,4aRS,6SR,8aRS)-decahydro 6-[1(2)H-tetrazole-5 ylmethyl]-3-isoquinolinecarboxylic acid, or a pharmaceutically acceptable salt thereof.

9. The method of claim 2 wherein the competitive NMDA antagonist is (3S,4aR,6S,8aR)-decahydro-6-[1(2)H-tetrazole-5-ylmethyl]-3-isoquinolinecarboxylic acid, or a pharmaceutically acceptable salt thereof.

10. The method of claim 1 wherein the competitive NMDA antagonist is a compound of the formula

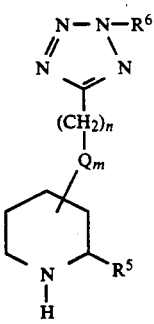

II wherein
the compound is in the 2R form;
$R^5$ is $CO_2R^7$, $CON(R^8)_2$, $CONHSO_2R^7$, $CONHCOR^7$, or

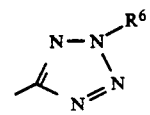

$R^6$ is hydrogen or $C_1$–$C_3$ alkyl;
n is 0, 1, 2, or 3;
m is 0 or 1;
$R^7$ is hydrogen, $C_1$–$C_4$ alkyl, phenyl, or an oral ester forming group;
Q is CH=;
each $R^8$ is independently hydrogen, $C_1$–$C_4$ alkyl, or phenyl; or
a pharmaceutically acceptable salt thereof.

11. The method of claim 10 wherein $R^5$ is $CO_2R^7$; $R^6$ is hydrogen or methyl; $R^7$ is hydrogen, $C_1$–$C_4$ alkyl, or phenyl; m is 0 or 1; and n is 1, 2, or 3; or a pharmaceutically acceptable salt thereof.

12. The method of claim 11 wherein $R^5$ is $CO_2H$; $R^6$ is hydrogen; m is 0; and n is 1, 2, or 3, or a pharmaceutically acceptable salt thereof.

13. The method of claim 12 wherein n is 1, or a pharmaceutically acceptable salt thereof.

14. The method of claim 10 wherein the competitive NMDA antagonist is (2SR,4RS)-cis-4-[(1(2)H-tetrazole 5-yl)methyl]-2-piperidinecarboxylic acid, or a pharmaceutically acceptable salt thereof.

15. The method of claim 10 wherein the competitive NMDA antagonist is (2R,4S)-cis-4 [(1(2)H-tetrazole-5-yl)methyl]-2-piperidinecarboxylic acid, or a pharmaceutically acceptable salt thereof.

* * * * *

UNITED STATES PATENT AND TRADEMARK OFFICE
CERTIFICATE OF CORRECTION

PATENT NO. : 5,192,751
DATED : March 9, 1993
INVENTOR(S) : Karl B. Thor

It is certified that error appears in the above-indentified patent and that said Letters Patent is hereby corrected as shown below:

Column 9, line 10, "$PO_{O3}H_2$, or tetrazole" should read --$PO_3H_2$, or tetrazole--.

Column 9, line 12, "$R^3$ is $C_1-C_{16}$ alkyl, benzyl, Or $C_1-C_5$" should read -- $R^3$ is $C_1-C_{16}$ alkyl, benzyl, or $C_1-C_5$--.

Column 9, line 24, "NMDA antagonists is (3SR,4aRS,6SR,8aRS)" should read -- NMDA antagonists is (3*SR*,4a*RS*,6*SR*,8a*RS*)--.

Column 9, line 31, "NMDA antagonists is (3S,4aR,6S,8aR)" should read -- NDMA antagonists is (3*S*,4a*R*,6*S*,8a*R*)--.

Column 9, line 33, "-(phosphonomethyl)-3 isoquinolinecarboxylic" should read -- -(phosphonomethyl)-3-isoquinolinecarboxylic--.

Column 9, line 38, "(3SR,4aRS,6SR,8aRS)-decahydro 6-[1(2)H-tetrazole-5 ylmethyl]-3-isoquinolinecarboxylic" should read --(3*SR*,4a*RS*,6*SR*,8a*RS*)- decahydro-6-[1(2)*H*-tetrazole-5-ylmethyl]-3-isoquinolinecarboxylic--.

UNITED STATES PATENT AND TRADEMARK OFFICE
CERTIFICATE OF CORRECTION

PATENT NO. : 5,192,751
DATED : March 9, 1993
INVENTOR(S) : Karl B. Thor

It is certified that error appears in the above-indentified patent and that said Letters Patent is hereby corrected as shown below:

Column 9, line 45, "(3S,4aR,6S,8aR)-decahydro-6-[1(2)H-tetrazole-5-ylmethyl]-3-isoquinolinecarboxylic" should read --(3*S*,4a*R*,6*S*,8a*R*)-decahydro-6-[1(2)*H*-tetrazole-5-ylmethyl]-3-isoquinolinecarboxylic--.

Column 10, line 16, "the compound is in the 2R form;" should read --the compound is in the 2*R* form;--.

Column 10, line 45, "(2SR,4RS)-cis-4-[(1(2)H-tetrazole 5-yl)methyl]-2-piperidinecarboxylic" should read --(2*SR*,4*RS*)-cis-4-[(1(2)*H*-tetrazole-5-yl)methyl]-2-piperidinecarboxylic--.

Column 10, line 49, "(2R,4S)-cis-4 [(1(2)H-tetrazole-5-yl)methyl]-2-piperidinecarboxylic" should read --(2*R*,4*S*)-cis-4-[(1(2)*H*-tetrazole-5-yl)methyl]-2-piperidinecarboxylic--.

Signed and Sealed this

Third Day of May, 1994

*Attest:*

BRUCE LEHMAN

*Attesting Officer*        *Commissioner of Patents and Trademarks*